(12) United States Patent
Honda et al.

(10) Patent No.: US 7,588,336 B2
(45) Date of Patent: Sep. 15, 2009

(54) OPHTHALMIC APPARATUS

(75) Inventors: Naoto Honda, Okazaki (JP); Yoshiaki Mimura, Gamagori (JP)

(73) Assignee: Nidek Co., Ltd., Gamagori-Shi (JP)

( * ) Notice: Subject to any disclaimer, the term of this patent is extended or adjusted under 35 U.S.C. 154(b) by 262 days.

(21) Appl. No.: 11/795,811

(22) PCT Filed: Mar. 3, 2006

(86) PCT No.: PCT/JP2006/004118

§ 371 (c)(1),
(2), (4) Date: Jul. 23, 2007

(87) PCT Pub. No.: WO2006/093280

PCT Pub. Date: Sep. 8, 2006

(65) Prior Publication Data

US 2008/0117383 A1 May 22, 2008

(30) Foreign Application Priority Data

Mar. 4, 2005 (JP) ............................. 2005-061346

(51) Int. Cl.
*A61B 3/14* (2006.01)
*A61B 3/10* (2006.01)
(52) U.S. Cl. ....................................... 351/208; 351/205
(58) Field of Classification Search ................. 351/205, 351/208
See application file for complete search history.

(56) References Cited

U.S. PATENT DOCUMENTS

| 5,463,430 | A | 10/1995 | Isogai et al. |
| 5,907,388 | A | 5/1999 | Fujieda |
| 6,131,574 | A * | 10/2000 | Kohayakawa ............... 600/401 |
| 6,537,215 | B2 * | 3/2003 | Miwa ......................... 600/405 |
| 7,399,081 | B2 * | 7/2008 | Mimura et al. ............. 351/205 |
| 2004/0189936 | A1 | 9/2004 | Mimura et al. |

FOREIGN PATENT DOCUMENTS

| EP | 0 310 045 A1 | 4/1989 |
| EP | 0 850 591 A1 | 7/1998 |
| EP | 1 464 272 A1 | 10/2004 |
| JP | A 4-144536 | 5/1992 |
| JP | A 6-46999 | 2/1994 |
| JP | A 10-108836 | 4/1998 |
| JP | A 2000-254098 | 9/2000 |
| JP | A 2002-172090 | 6/2002 |
| JP | A 2003-126038 | 5/2003 |
| JP | A 2004-313758 | 11/2004 |

* cited by examiner

*Primary Examiner*—Jordan M. Schwartz
(74) *Attorney, Agent, or Firm*—Oliff & Berridge, PLC

(57) ABSTRACT

An apparatus that includes an intraocular pressure measurement part having a blowing unit, an optical characteristics measurement part, a main body having the above measurement parts, a measurement part shifting unit bringing one of the measurement parts to a measurable state, a working distance detecting unit having a projection optical system and a photo-receiving optical system, a control part judging whether to continue shifting the intraocular pressure measurement part to the measurable state based on a detection result and controlling the shifting unit based on a judgment result, and a detection unit directly or indirectly detecting whether light photo-received on the photo-receiving optical system is target light reflected from a cornea, wherein when the light is not the target light, the control part judges it proper to continue shifting and controls the shifting unit.

6 Claims, 4 Drawing Sheets ized by US 7,588,336 B2

OPHTHALMIC APPARATUS

TECHNICAL FIELD

The present invention relates to an ophthalmic apparatus capable of measuring a plurality of different eye characteristics of an examinee's eye, and specifically relates to an ophthalmic apparatus capable of measuring intraocular pressure and optical characteristics such as eye refractive power of an examinee's eye.

BACKGROUND ART

An apparatus capable of measuring intraocular pressure and optical characteristics such as eye refractive power and a corneal shape of an examinee's eye is proposed (see US 2004/0189936 A1 (Japanese Patent Application Unexamined Publication 2004-313758)). In this apparatus, such a mechanism is provided that optically detects a working distance of the apparatus with respect to the eye so as to prevent a nozzle for blowing air for intraocular pressure measurement on the eye from making contact with the eye. When the detected working distance become equal to or shorter than a predetermined working distance, control such as stopping a changeover from optical characteristics measurement to intraocular pressure measurement is performed so as to prevent the nozzle from making contact with the eye. However, due to entering of disturbance light and other reasons, it is sometimes unintentionally judged that the nozzle could make contact with the eye even if an examinee is not actually in front of the apparatus.

DISCLOSURE OF THE INVENTION

Problem to Be Solved by the Invention

The present invention has been made in view of the above circumstances and has an object to overcome the above problems and to provide an ophthalmic apparatus capable of efficiently measuring a plurality of different eye characteristics while avoiding a misjudgment.

Means for Solving the Problems

To solve the above problems, the present invention is characterized as having configurations described below.

An ophthalmic apparatus capable of measuring a plurality of different eye characteristics of an examinee's eye includes an intraocular pressure measurement part which measures intraocular pressure of the eye, including a blowing unit which blows fluid on a cornea of the eye via a nozzle, an optical characteristics measurement part which measures optical characteristics of the eye, a main body in which the intraocular measurement part and the optical characteristics measurement part are provided, a measurement part shifting unit which brings any one of the intraocular measurement part and the optical characteristics measurement part to a measurable state, a working distance detecting unit which optically detects a working distance of the apparatus with respect to the eye at the time of bringing the intraocular pressure measurement part to the measurable state, including a projection optical system for projecting target light onto the cornea, and a photo-receiving optical system for photo-receiving the target light reflected from the cornea, a control part which judges whether it is proper to continue shifting the intraocular pressure measurement part to the measurable state based on a detection result on the working distance, and controls the measurement part shifting unit based on a result of the judgment, and a detection unit which directly or indirectly detects whether or not light photo-received on the photo-receiving optical system is the target light reflected from the cornea, wherein when the detection unit detects that the light photo-received on the photo-receiving optical system is not the target light reflected from the cornea, the control part judges it proper to continue shifting the intraocular pressure measurement part to the measurable state regardless of the detection result on the working distance, and controls the measurement part changeover unit to continue the shifting.

BEST MODE FOR CARRYING OUT THE INVENTION

Figure 1:
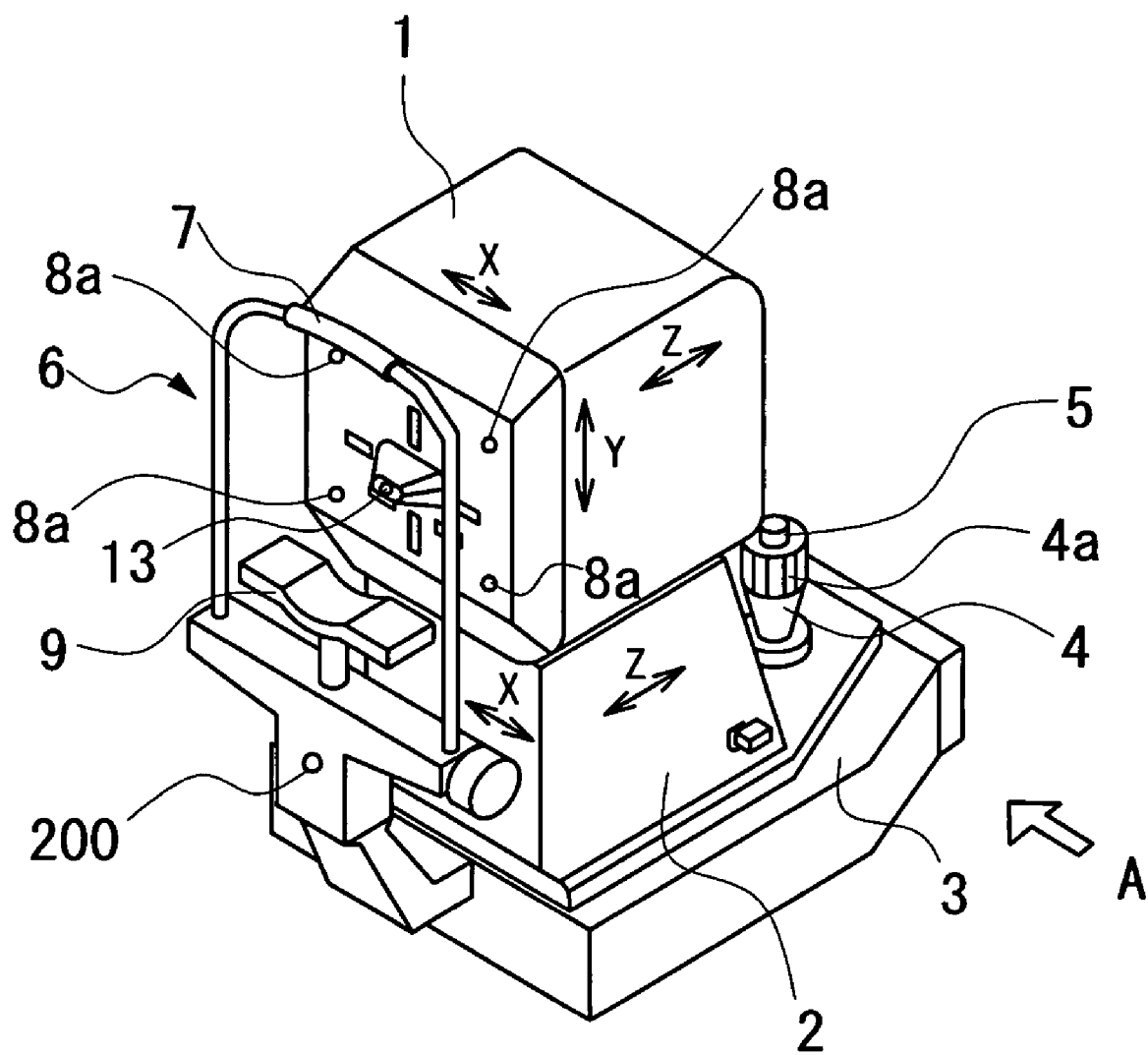
FIG. 1 is a view showing a schematic configuration of an ophthalmic apparatus according to the preferred embodiment of the present invention.

A detailed description of one preferred embodiment of the present invention is provided below with reference to the accompanying drawings. In this preferred embodiment, a multifunction apparatus which measures intraocular pressure and eye refractive power is taken as an example. FIG. 1 is a view showing a schematic configuration of an ophthalmic apparatus according to the preferred embodiment of the present invention.

A moving base 2 is placed on a base 3 to be movable in a right-and-left direction (hereinafter, referred to as an X-direction) and in a back-and-forth direction (a direction of a working distance, hereinafter, referred to as a Z-direction). Movement of the moving base 2 is mechanically (or electrically) performed by tilting operation of a joystick 4. In addition, a main body 1 is placed on the moving base 2 to be movable in the X-direction, the Z-direction and an up-and-down direction (hereinafter, referred to as a Y-direction) by driving of a moving unit 130. In addition, movement of the main body 1 in the Y-direction is electrically performed also by operation of a rotating knob 4a of the joystick 4.

A face supporting unit 6 for supporting a face (a head) of an examinee is fixed to the base 3. A measurement starting switch 5 is placed at the top of the joystick 4. A projection window 8a is for transmitting light from an infrared light source 20 for anterior segment illumination.

A sensor 200 is for detecting whether or not the examinee is in front of the apparatus (on the face supporting unit 6 side of the apparatus) (an examinee sensor). In this preferred embodiment, a sensor for measuring a distance from the apparatus to the examinee by using an ultrasonic wave is employed, which is provided facing toward the examinee side of the apparatus, and in this preferred embodiment, the sensor 200 is provided at a lower part of the face supporting unit 6. A known distance sensor such as an optical distance sensor may be employed instead of the ultrasonic distance sensor. In addition, a sensor which detects whether or not the examinee is brought into contact with a part of the apparatus may be employed instead of the sensor which measures the distance from the apparatus to the examinee. For example, it is preferable to provide a forehead rest 7 and/or a chin rest 9 of the face supporting unit 6 with touch sensors and detect whether or not the examinee is in front of the apparatus based on a result of detection by the touch sensors.

Figure 2:
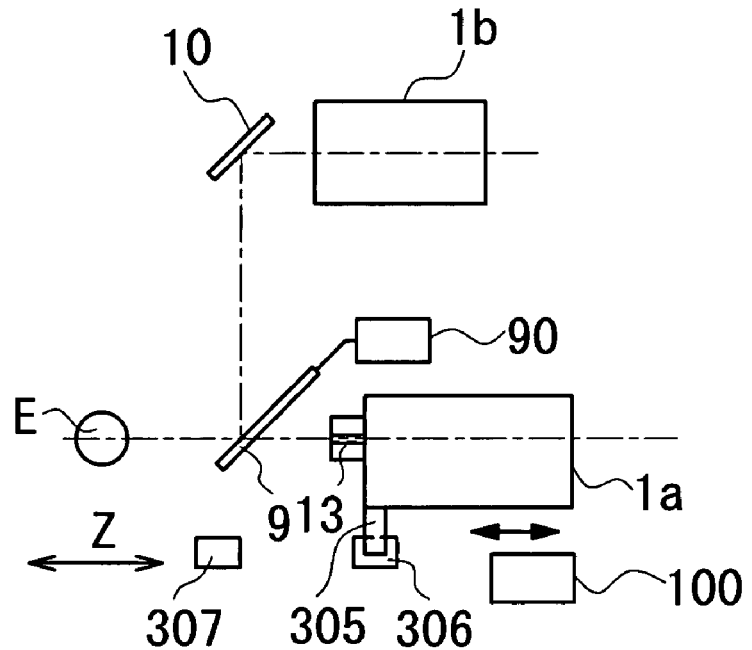
FIGS. 2A and 2B are views showing a schematic configuration of the inside of a main body of the apparatus when viewed from a lateral direction.
Figure 2:
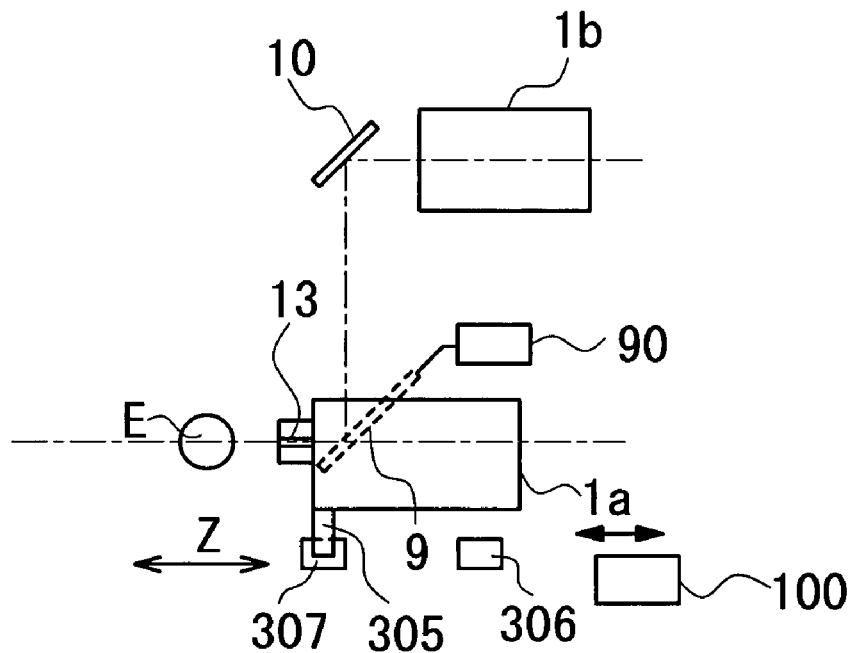

FIGS. 2A and 2B are views showing a schematic configuration of the inside of the main body 1 when viewed from a lateral direction (a direction of an arrow A in FIG. 1). In the main body 1, an intraocular pressure measurement part 1*a* for performing noncontact measurement of intraocular pressure of an examinee's eye E is arranged to be movable in the Z-direction, and an eye refractive power measurement part 1*b* for performing measurement of eye refractive power of the eye E, that is an optical characteristics measurement part, is fixed to be located on the intraocular pressure measurement part 1*a*. In addition, a reflecting mirror 9, a reflecting mirror 10, a mirror moving unit 90 and an intraocular pressure measurement part moving unit 100 are provided.

The measurement part 1*a* is brought into parallel movement in the Z-direction by the moving unit 100. The moving unit 90 inserts and removes the mirror 9 between the eye E and a nozzle 13 included in the measurement part 1*a* in response to the movement of the measurement part 1*a* in the Z-direction. To be specific, when the measurement part 1*a* is moved from a retreat position in FIG. 2A to a measurement reference position in FIG. 2B, the mirror 9 is moved from a state of being inserted in front of the nozzle 13 (between the eye E and the nozzle 13) to a state of being removed therefrom. When the measurement part 1*a* is moved from the measurement reference position in FIG. 2B to the retreat position in FIG. 2A, the mirror 9 is moved from the removed state to the inserted state. With the above-described configuration, one of the measurement part 1*a* and the measurement part 1*b* is brought to a measurable state. That is to say, a measurement part shifting unit is configured by the moving unit 90 and the moving unit 100.

A shielding plate 305 is attached to the measurement part 1*a*. When the shielding plate 305 is detected by a photosensor 306, a calculation and control part 110 detects that the measurement part 1*a* is moved to the retreat position in FIG. 2A. When the shielding plate 305 is detected by a photosensor 307, the calculation and control part 110 detects that the measurement part 1*a* is moved to the measurement reference position in FIG. 2B.

Figure 3:
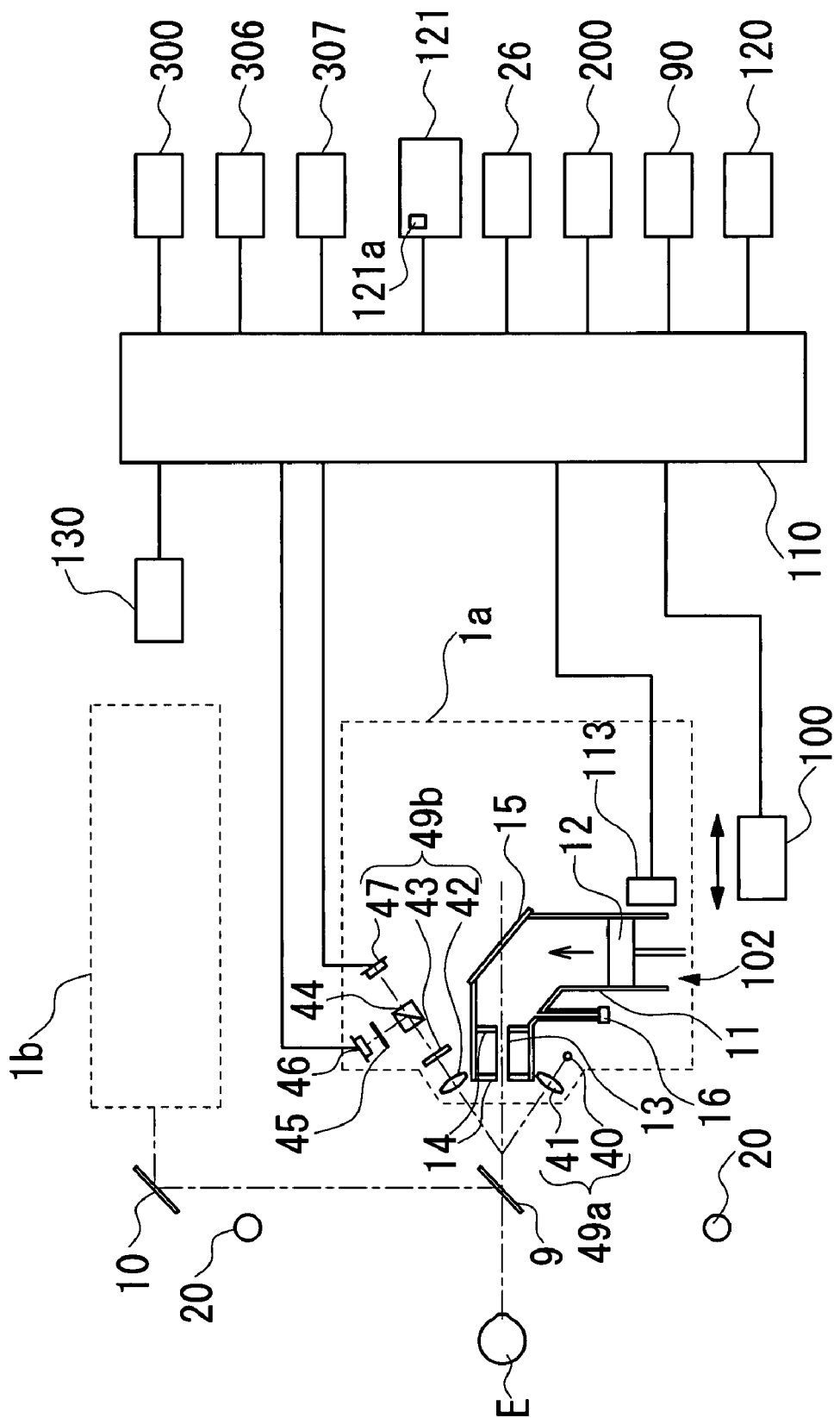
FIG. 3 is a view showing a schematic configuration of an intraocular pressure measurement part and a control system.

FIG. 3 is a view showing a schematic configuration of the measurement part 1*a* and a control system. An air (fluid) blowing unit 102 includes a cylinder 11, a piston 12, a rotary solenoid 113, and the like. An air compressed inside the cylinder 11 by movement of the piston 12 by a driving force of the solenoid 113 is blown on a cornea of the eye E from the nozzle 13. Two transparent glass plates 14 hold the nozzle 13. A transparent glass plate 15 is provided behind the nozzle 13. An optical system for detecting alignment states in the X- and Y-directions and the like are arranged behind the glass plate 15. A pressure sensor 16 detects pressure inside the cylinder 11.

Target light for corneal deformation state detection from an infrared light source 40 is made into an approximately parallel light bundle by a collimator lens 41 to be projected onto the cornea. A corneal reflection image of the light source 40 (the target light reflected from the cornea) is photo-received on a photodetector 46 via a photo-receiving lens 42, a filter 43, a half mirror 44 and a pinhole plate 45. The filter 43 has properties of transmitting the light from the light source 40 and not transmitting the light from the light source 20. A corneal deformation state detecting optical system (an intraocular pressure measurement optical system) configured by the above components is arranged so that a photo-receiving amount of the photodetector 46 is maximized when the cornea is in a predetermined deformation state (a flattened state).

In addition, the target light from the light source 40 is made into the approximately parallel light bundle by the lens 41 to be projected onto the cornea (an alignment target light projection optical system 49*a* is configured by the light source 40 and the lens 41), and the corneal reflection image of the light source 40 (the target light reflected from the cornea) is photo-received on a photodetector 47 that is a position detector such as a PSD, or a line sensor, via the lens 42 to the half mirror 44 (an alignment target light photo-receiving optical system 49*b* is configured by the lens 42, the filter 43 and the photodetector 47). When the eye E is moved in the Z-direction, an incident position of the corneal reflection image of the light source 40 is also moved on the photodetector 47; therefore, an alignment state of the apparatus (the measurement part 1*a*) with respect to the eye E in the Z-direction can be detected based on a signal outputted from the photodetector 47.

A Z-direction alignment state detecting optical system including the projection optical system 49*a* and the photo-receiving optical system 49*a* doubles as an optical system for detecting a working distance of the apparatus with respect to the eye E to prevent the nozzle 13 from making contact with the eye E and the like when the measurement part 1*a* is brought to the measurable state in response to a signal for shifting the apparatus from an eye refractive power measurement mode to an intraocular pressure measurement mode (details will be described later). These optical systems may be constituted separately.

In addition, FIG. 3 illustrates that the corneal deformation state detecting optical system and the working distance detecting optical system (the Z-direction alignment state detecting optical system) are actually arranged in a vertical direction (the Y-direction); however, they are arranged in a horizontal direction (the X-direction). In addition, the measurement part 1*a* includes known configurations such as an optical system for detecting alignment states of the apparatus (the measurement part 1*a*) with respect to the eye E in the X- and Y-directions, an optical system for presenting a fixation target to the eye E and an optical system for observing an anterior segment of the eye E.

The measurement part 1*b* includes an optical system for projecting target light for eye refractive power measurement onto a fundus of the eye E and measuring eye refractive power based on a photo-receiving result of the target light reflected from the fundus (for more details of the eye refractive power measurement optical system, see U.S. Pat. No. 5,907,388 (Japanese Patent Application Unexamined Publication Hei10-108836)). In addition, the measurement part 1*b* includes known configurations such as an optical system for detecting alignment states of the apparatus (the measurement part 1*b*) with respect to the eye E in the X-, Y- and Z-directions, an optical system for presenting a fixation target to the eye E, and an optical system for observing the anterior segment of the eye E.

The calculation and control part 110, which performs control of the entire apparatus, calculation of a measurement value and the like, is connected with the moving unit 90, the moving unit 100, the moving unit 130, the solenoid 113, the photodetector 46, the photodetector 47, a monitor 26, a memory 120, a switch part 121 having a measurement mode selecting switch 121*a* for selecting any one of the intraocular pressure measurement mode and the eye refractive power measurement mode and the like, the sensor 200, the photosensor 306, the photosensor 307, a micro switch 300, and the like.

Figure 4:
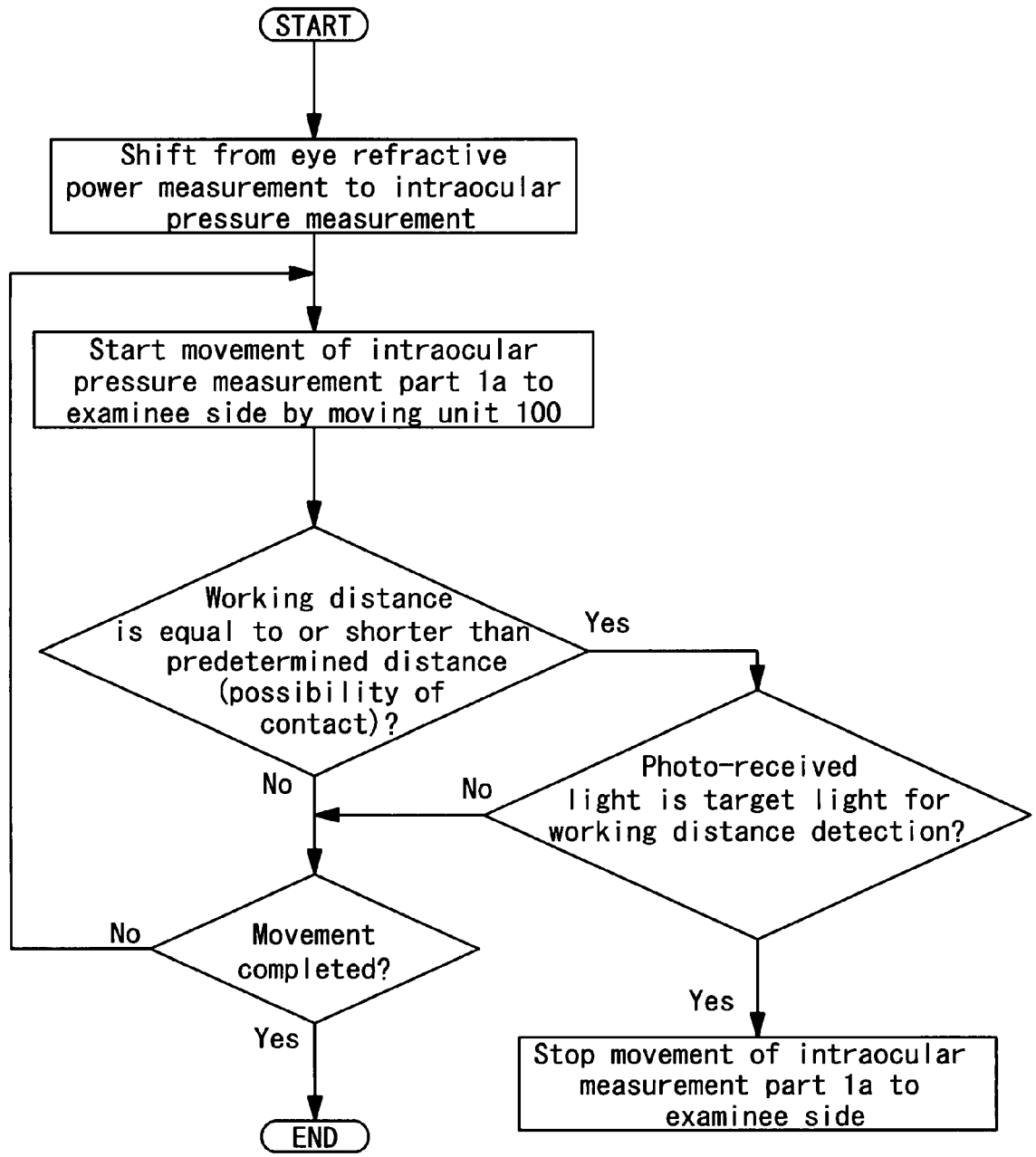
FIG. 4 is a flow chart showing operations to bring the intraocular pressure measurement part to a measurable state.

A detailed description will be given to operation of the apparatus having the above-described configuration with reference to a flow chart in FIG. 4. When the intraocular pressure measurement and the eye refractive power measurement are successively performed, the eye refractive power measurement is ordinarily performed first. This is because if the intraocular pressure measurement comes first, there is a possibility that blowing the compressed air and the like have an influence on the subsequent eye refractive power measurement.

When the eye refractive power measurement is performed, predetermined conditions for measurement termination are satisfied, and the switch 121a is pressed, the calculation and control part 110 generates a signal for shifting the apparatus from the eye refractive power measurement mode to the intraocular pressure measurement mode (the calculation and control part 110 may automatically generate the shifting signal when the eye refractive power measurement is finished). When the apparatus is shifted to the intraocular pressure measurement mode from the eye refractive power measurement mode, the moving base 2 is moved away from the examinee by the operation of the joystick 4. Then, when the micro switch 300 detects that the moving base 2 is moved to the backmost position, the calculation and control part 110 drives and controls the moving unit 100 to move the measurement part 1a to the examinee side so as to bring the measurement part 1a to the measurable state.

In the course of the movement of the measurement part 1a to the examinee side, if a detection result on the working distance obtained by the working distance detecting optical system is judged to be equal to or shorter than a predetermined distance (e.g. 10 mm) and the sensor 200 detects that the examinee is in front of the apparatus (the examinee is within a predetermined distance (e.g. 40 cm) from the apparatus), the calculation and control part 100 controls to stop the movement of the measurement part 1a (the calculation and control part 100 may further control to move the measurement part 1a in a direction opposite to the examinee side so as to have the predetermined distance or more between the examinee and the apparatus). In other words, the calculation and control part 110 stops the operation for bringing the measurement part 1a to the measurable state. Then, a display to that effect is made on the monitor 26. In this case, since the examinee himself/herself acts as a shield against the disturbance light, it can be indirectly detected that the light photo-received on the photodetector 47 is the target light for working distance detection from the light source 40. Accordingly, it can be said that stopping the movement of the measurement part 1a is proper for preventing the nozzle 13 from making contact with the eye E.

On the other hand, in the course of the movement of the measurement part 1a to the examinee side, if the detection result on the working distance is judged to be equal to or shorter than the predetermined distance but the sensor 200 detects that the examinee is not in front of the apparatus (the examinee is not within the predetermined distance from the apparatus), the calculation and control part 110 controls to continue the movement of the measurement part 1a regardless of the detection result on the working distance. In this case, it can be indirectly detected that the light photo-received on the photodetector 47 is not the target light from the light source 40. Since the examinee is not in front of the apparatus to begin with, the nozzle 13 could not make contact with the eye E.

When the photosensor 307 detects that the measurement part 1a is moved to the measurement reference position in the course of the movement of the measurement part 1a to the examinee side, the calculation and control part 110 controls to stop the movement of the measurement part 1a. Accordingly, the measurement part 1a is brought to the measurable state.

When the measurement part 1a is brought to the measurable state and the alignment with respect to the eye E is completed as described above, a trigger signal for measurement start is generated with the switch 5 (or automatically), and the solenoid 113 is driven via an unillustrated driving circuit. The air compressed inside the cylinder 11 by the movement of the piston 12 by the driving force of the solenoid is blown on the cornea from the nozzle 13. The cornea is gradually deformed by the blow of the air, and a photo-receiving amount of the photodetector 46 is maximized when the cornea reaches a predetermined deformation state. The calculation and control part 110 calculates the intraocular pressure based on a signal outputted from the pressure sensor 16 and a signal outputted from the photodetector 46.

With the above-described configuration, it can be indirectly detected whether or not the light photo-received on the photodetector 47 is the target light from the light source 40; therefore, it is possible to prevent the measurement part 1a from being stopped due to an influence by the disturbance light and the like during the movement of the measurement part 1a to the examinee side by shifting the apparatus from the eye refractive power measurement mode to the intraocular pressure measurement mode.

Incidentally, in this preferred embodiment, based on a result of the measurement (the detection) by the sensor 200, it is indirectly detected whether or not the light photo-received on the photodetector 47 is the target light from the light source 40; however, a configuration described below may be employed. To be specific, in the course of the movement of the measurement part 1a to the examinee side for bringing the measurement part 1a to the measurable state, if the detection result on the working distance obtained by the working distance detecting optical system is judged to be equal to or shorter than the predetermined distance, the calculation and control part 110 controls to suspend the projection of the target light from the light source 40. If, nevertheless, the detection result on the working distance is still judged to be equal to or shorter than the predetermined distance, it is turned out that the light photo-received on the photodetector 47 is not the target light from the light source 40, and accordingly, the calculation and control part 110 controls to continue the movement of the measurement part 1a regardless of the detection result on the working distance. With the above-described configuration, it can be directly detected whether or not the light photo-received on the photodetector 47 is the target light from the light source 40; therefore, it is possible to prevent the movement of the measurement part 1a to the examinee side from being stopped due to the influence of the disturbance light, and the like.

Incidentally, in this preferred embodiment, the eye refractive power measurement part is used as the optical characteristics measurement part; however, the present invention is not limited thereto. A part which measures the optical characteristics of the examinee's eye such as a corneal shape measurement part, an eye refractive power and corneal shape measurement part, an axial length measurement part or the like may be used as the optical characteristics measurement part. In addition, the measurement of the optical characteristics of the examinee's eye should include photographing the fundus, the anterior segment or the like of the examinee's eye.

The invention claimed is:

1. An ophthalmic apparatus capable of measuring a plurality of different eye characteristics of an examinee's eye, the apparatus comprising:

an intraocular pressure measurement part which measures intraocular pressure of the eye, the intraocular pressure measurement part including a blowing unit which blows fluid on a cornea of the eye via a nozzle;

an optical characteristics measurement part which measures optical characteristics of the eye;

a main body in which the intraocular measurement part and the optical characteristics measurement part are provided;

a measurement part shifting unit which brings any one of the intraocular measurement part and the optical characteristics measurement part to a measurable state;

a working distance detecting unit which optically detects a working distance of the apparatus with respect to the eye at the time of bringing the intraocular pressure measurement part to the measurable state, including
  a projection optical system for projecting target light onto the cornea, and
  a photo-receiving optical system for photo-receiving the target light reflected from the cornea;

a control part which judges whether it is proper to continue bringing the intraocular pressure measurement part to the measurable state based on a detection result on the working distance, and controls the measurement part shifting unit based on a result of the judgment; and a detection unit which directly or indirectly detects whether or not light photo-received on the photo-receiving optical system is the target light reflected from the cornea, wherein when the detection unit detects that the light photo-received on the photo-receiving optical system is not the target light reflected from the cornea, the control part judges it proper to continue bringing the intraocular pressure measurement part to the measurable state regardless of the detection result on the working distance, and controls the measurement part shifting unit to continue the bringing.

2. The ophthalmic apparatus according to claim 1, wherein the detection unit detects whether or not the examinee is in front of the apparatus, and detects whether or not the light photo-received on the photo-receiving optical system is the target light reflected from the cornea based on a result of the detection.

3. The ophthalmic apparatus according to claim 2, wherein the detection unit includes a sensor which measures a distance from the apparatus to the examinee.

4. The ophthalmic apparatus according to claim 2, wherein the detection unit includes a sensor which detects whether or not the examinee is brought into contact with a part of the apparatus.

5. The ophthalmic apparatus according to claim 1, wherein, based on a comparison between a photo-receiving state of the photo-receiving optical system in receiving the projected target light and a photo-receiving state of the photo-receiving optical system in not receiving the projected target light, the detection unit directly detects whether or not the light photo-received on the photo-receiving optical system is the target light reflected from the cornea.

6. The ophthalmic apparatus according to claim 1, wherein:
  the intraocular pressure measurement part is arranged to be movable in the main body; and
  the measurement part shifting unit moves the intraocular pressure measurement part to an examinee's eye side to bring the intraocular pressure measurement part to the measurable state.

* * * * *

UNITED STATES PATENT AND TRADEMARK OFFICE
CERTIFICATE OF CORRECTION

PATENT NO. : 7,588,336 B2
APPLICATION NO. : 11/795811
DATED : September 15, 2009
INVENTOR(S) : Naoto Honda et al.

Page 1 of 1

It is certified that error appears in the above-identified patent and that said Letters Patent is hereby corrected as shown below:

On Title page, please correct the following to read:

Item --(86)   PCT No.:   PCT/JP2006/304118--

Signed and Sealed this

Twenty-ninth Day of December, 2009

David J. Kappos
*Director of the United States Patent and Trademark Office*